United States Patent
Rodriguez Vilaboa

(10) Patent No.: US 12,016,894 B2
(45) Date of Patent: Jun. 25, 2024

(54) COMPOSITION FOR USE IN THE PREVENTION AND/OR TREATMENT OF THE GENITOURINARY MUCOSA

(71) Applicant: MUCOSA INNOVATIONS, S.L., Madrid (ES)

(72) Inventor: Deborah Rodriguez Vilaboa, Madrid (ES)

(73) Assignee: MUCOSA INNOVATIONS, S.L., Madrid (ES)

( * ) Notice: Subject to any disclaimer, the term of this patent is extended or adjusted under 35 U.S.C. 154(b) by 644 days.

(21) Appl. No.: 17/264,647

(22) PCT Filed: Jul. 31, 2019

(86) PCT No.: PCT/EP2019/070588
§ 371 (c)(1),
(2) Date: Jan. 29, 2021

(87) PCT Pub. No.: WO2020/025657
PCT Pub. Date: Feb. 6, 2020

(65) Prior Publication Data
US 2021/0322505 A1 Oct. 21, 2021

(30) Foreign Application Priority Data
Jul. 31, 2018 (EP) .................. 18382576

(51) Int. Cl.
*A61K 36/63* (2006.01)
*A61K 31/047* (2006.01)
*A61K 31/205* (2006.01)
*A61P 15/02* (2006.01)

(52) U.S. Cl.
CPC ............ *A61K 36/63* (2013.01); *A61K 31/047* (2013.01); *A61K 31/205* (2013.01); *A61P 15/02* (2018.01)

(58) Field of Classification Search
None
See application file for complete search history.

(56) References Cited

U.S. PATENT DOCUMENTS 8,540,970 B2   9/2013   Rodriguez-Vilaboa

FOREIGN PATENT DOCUMENTS

| EP | 1444984 A1 | 8/2004 |
| WO | WO 02/47692 A1 | 6/2002 |
| WO | WO 2007/085020 A2 | 7/2007 |

OTHER PUBLICATIONS

Martin et al., "Products based on olive oil, betaine, and xylitol in the post-radiotherapy xerostomia." Rep Pract Oncol Radiother. Jan-Feb. 2017; 22(1):71-76.
Palacios et al., "Update on management of genitourinary syndrome of menopause: A practical guide." Maturitas. Nov. 2015; 82(3):308-13.
Portman, "Genitourinary Syndrome of Menopause: New Terminology for Vulvovaginal Atrophy from the International Society for the Study of Women's Sexual Health and The North American Menopause Society." J Sex Med 2014;11:2865-2872.

*Primary Examiner* — Michael V Meller
(74) *Attorney, Agent, or Firm* — Casimir Jones SC; Lisa Mueller

(57) ABSTRACT

The present invention refers to a composition for use in the prevention and/or treatment of a medical condition affecting the urogenital mucosa. It also refers to the use of said composition for preparing a medicament for the prevention and/or treatment of said condition. Furthermore, it refers to a method of preventing and/or treating said condition in which said composition is administered to a subject in need thereof.

12 Claims, 1 Drawing Sheet

COMPOSITION FOR USE IN THE PREVENTION AND/OR TREATMENT OF THE GENITOURINARY MUCOSA

CROSS-REFERENCE TO RELATED APPLICATIONS

This application is a national phase application under 35 U.S.C. § 371 of PCT International Application No. PCT/EP2019/070588, filed Jul. 31, 2019, which claims the benefit of European Application No. 18382576.9, filed Jul. 31, 2018, each of which are herein incorporated by reference.

FIELD OF THE INVENTION

The present invention refers to the field of therapy, in particular, it refers to a composition for use in the prevention and/or treatment of a condition affecting the genitourinary mucosa.

BACKGROUND OF THE INVENTION

The mucous membrane, so called mucosa, is a continuity of the human skin at the orifices or osculum of the body such as ears, nose, mouth, lips, anus, eyes and the genitourinary system (also known as urogenital system).

The mucosa behaves as a defensive barrier yet has absorptive functions and has a resistance towards friction, acids and other excretions that are indispensable for normal human functions. It is a microbiome carrier and subject to pH and microflora shifts. Integrity and normal equilibrium of this mucous membrane is also a barrier for pathogens. Research trend in the last years relates mucosa to the immune system and general wellbeing.

Different factors negatively affect the genitourinary mucosa, such as estrogen deficiency, cancer treatments, aging, smoking, etc., and can result in, amongst others, urogenital atrophy.

Urogenital atrophy is also known as vaginal atrophy, atrophic vaginitis, atrophic vulvo vaginitis, and vulvovaginal atrophy (VVA). More recently, the name Genitourinary Syndrome of Menopause (GSM) has been proposed instead of VVA (Portman D J, Gass M L. Vulvovaginal atrophy terminology consensus conference panel. Genitourinary syndrome of menopause: new terminology for vulvovaginal atrophy from the international society for the study of women's sexual health and the North American Menopause Society. J Sex Med. 2014 December; 11(12):2865-72). The aims of the new terminology were to describe the condition appropriately for medical care, teaching, and research. GSM is a more descriptive term than VVA and does not imply pathology (e.g. patients do not associate it straightaway with having a disease, though GSM has pathological symptoms). GSM is defined as a collection of symptoms and sings associated with a decrease in estrogen and other sex steroids involving changes to the labia majora/minora, clitoris, vestibule/introitus, vagina, urethra and bladder (Portman and Gass, 2014). GSM is a chronic condition that requires long term therapy.

Even though the new term GSM mentions "menopause", this syndrome is not limited to peri-, post-menopause women, as it can occur in young women due to estrogen deficiency arising from, amongst others, cancer treatment, oophorectomy, chemically-induced menopause, smoking, or sex-change treatments. It is worth recalling that breast cancer, in its most aggressive version, occurs in premenopausal women between the ages of 30 and 45 and approximately 50% of the women receiving oncologic treatment (e.g. tamoxifen, tamoxifen in combination with aromatase inhibitors) develop VVA. Thus, the authors of the present invention, in view of this, propose a second term, Genitourinary Syndrome (GS, hereinafter), which is used in the present invention to make clear that this syndrome is not limited to peri-, post-menopause women.

Women experiencing GS often present with both sexual and nonsexual or urologic complications due to a deficiency in the normal level of estrogen, which affects many organs including the genitourinary system. With estrogen loss, even that one caused by aging, the vagina shortens, narrows, and the mucosa vaginal walls become thinner, flatter, less elastic and pale in color. Numerous symptoms accompany these changes. Typically, women with GS experience one, more, or all of the following symptoms: vaginal dryness, postcoital bleeding, vaginal discharge, vaginal and/or vulvar discomfort, vaginal and/or vulvar pain, soreness, loss of sexual arousal and libido, itching, irritation, burning sensation, vulvar pruritus, and dyspareunia. The epithelial changes in the urinary mucosa of the bladder, ureters and urethra are similar to those occurring in the vagina and result in thin, pale, friable tissue. Specifically, urinary symptoms associated with GS include urinary urgency, increased frequency, nocturia, dysuria, and incontinence. Many women with GS experience significant personal distress and loss of quality of life due to the pain associated with the disorder, the inconvenience associated with the urological symptoms, and the potential interruption in personal relationships associated with the resultant sexual dysfunction. This latter is even more relevant in younger women with active sexual life in other what healthy conditions.

Despite all these symptoms and their important impact on the quality of life, GS is underreported and underdiagnosed. Moreover, even though GS has been intensively studied in women, the urogenital atrophic changes that negatively affect urethra, ureters and bladder can take place both in females and males. In fact, in males it has been described the thinning of the mucosa walls along the urethra, prostatic urethra and lower part of the bladder. Thus, in the present invention GS also applies to males.

Current modalities for the treatment of atrophic vaginitis generally revolve around the use of hormonal agents. Medications containing the female hormone estrogen have been widely prescribed, both systemically (oral and parenteral forms) and in topical applications, including creams, vaginal rings, and vaginal tablets. Examples of patent documents disclosing hormonal treatments of atrophic vaginitis are WO 02/47692 A1 and WO 2007/085020 A2. Unfortunately, the use of estrogen containing medications have significant drawbacks, including the increased risk of developing estrogen dependent neoplasms, breast sensitivity, nausea and vomiting, vaginal bleeding, and pain in the perineal area. The use of hormones topical applications, while reducing the risks of systemic exposure, is not without side effects including the development of hyperplasia and endometrial thickening.

Some of the associated side effects with the use of estrogen are an increased risk of stroke, and when estrogen is taken with progestin there is an increased risk of breast cancer, uterine cancer, stroke, heart attack, blood clots, dementia, gallbladder disease, and ovarian cancer. Treatments using estrogen may be suitable for some women, but are not suitable for women who, for example, are at risk of breast, uterine, endometrial, ovarian, or fallopian tube cancer or have had such cancer(s). Accordingly, there is a need for an effective therapeutic treatment of GS without exposing the patient to added estrogenic activity. Surprisingly, the authors of the present invention have developed such treatment.

OBJECT OF THE INVENTION

A first aspect of the present invention refers to a composition comprising olive oil, trimethylglycine (TMG) and xylitol for use in the prevention and/or treatment of a condition affecting the urogenital mucosa.

A second aspect of the present invention refers to the use of a composition comprising olive oil, TMG and xylitol for the preparation of a medicament for the prevention and/or treatment of a condition affecting the urogenital mucosa.

A third aspect of the present invention refers to a method of treating a condition affecting the urogenital mucosa in a subject in need thereof, comprising administering to the subject a therapeutically effective amount of a composition comprising olive oil, TMG and xylitol.

A fourth aspect of the present invention refers to a method of preventing a condition affecting the urogenital mucosa in a subject which comprises administering to the subject a prophylactically effective amount of a composition comprising olive oil, TMG and xylitol.

Other objects, features, advantages and aspects of the present application will become apparent to those skilled in the art from the following description and appended claims.

DETAILED DESCRIPTION OF THE INVENTION

Figure 1:
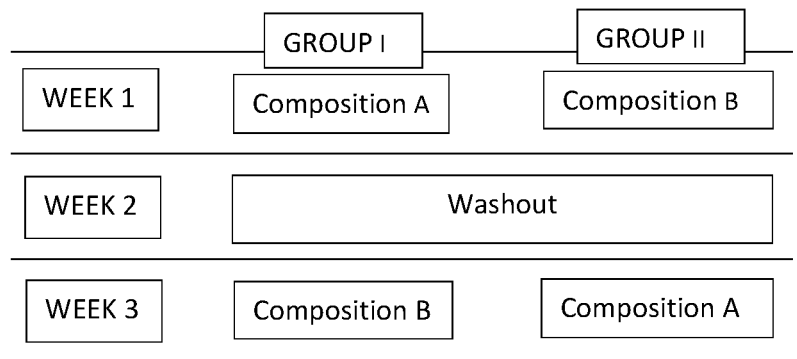
FIG. 1 shows the design of the study carried out in Example 1 (Study of prevention of GS). Subjects were separated into two groups, Group I and Group II. Group I received composition A on week 1 and composition B on week 3. Group II received composition B on week 1 and composition A on week 3. None of the groups received any treatment on week 2 (washout).
Figure 2:
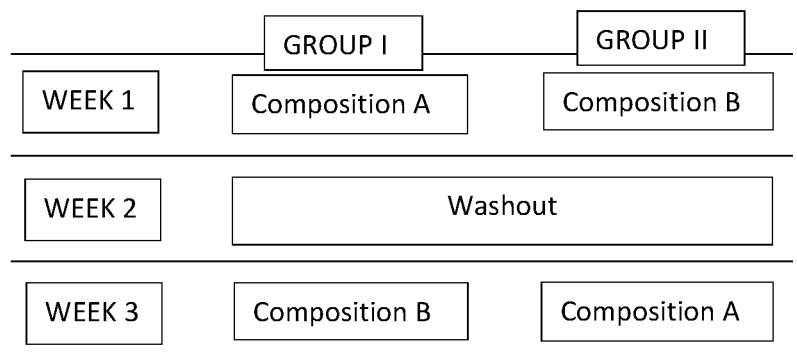
FIG. 2 shows the design of the study carried out in Example 2 (Comparative study of treatment of GS). Subjects were separated into two groups, Group I and Group II. Group I received composition A on week 1 and composition B on week 3. Group II received composition B on week 1 and composition A on week 3. None of the groups received any treatment on week 2 (washout).

As used herein, the singular forms "a", "an" and "the" include their corresponding plural forms unless the context clearly indicates otherwise. Unless defined otherwise, all the technical and scientific terms used herein have the same meaning as commonly understood by a person skilled in the art to which this invention belongs. To facilitate understanding and clarify the meaning of specific terms in the context of the present invention, the following definitions and particular and preferred embodiments thereof, applicable to all the embodiments of the different aspects of the present invention, are provided:

In the present invention, condition refers to a medical condition, i.e. a condition treatable by medicine or requiring medical treatment. In particular, it refers to a negative condition or disorder. More particularly, in the case of a condition affecting the urogenital mucosa, it refers to a condition negatively affecting the urogenital mucosa or a disorder (negatively) affecting the urogenital mucosa.

The urogenital mucosa is the mucosa of the genitourinary system, that includes the genital system and the urinary system. As mentioned above, the deficiency (e.g. partial or total loss) of estrogen negatively affects the urogenital mucosa. Thus, in a particular embodiment of the present invention (i.e. first, second, third, and fourth aspect of the invention), the condition affecting the urogenital mucosa (referred to as condition of the invention hereinafter) is a condition due to estrogen deficiency (i.e. a condition characterized by estrogen deficiency).

As explained above, the deficiency in estrogen results, amongst others, in thinning of the mucosa of the urogenital system. Thus, in another particular embodiment of the present invention, the condition affecting the urogenital mucosa is a condition characterized by a thinning of the urogenital mucosa.

In particular, the thinning of the vaginal mucosa provides less possibility of epithelium renewal and less production of important cell metabolites, particularly glycogen. Normally glycogen would provide a source of glucose which in thick normal mucosa would be converted to lactic acid by normal vagina's microbiome, mainly by the lactobacillus which in turn makes it possible for a low vaginal pH in the vagina to prevent most infections. If this natural mechanism is absent because of mucosa thinning in the atrophic vagina, pH changes from an ideal of 3.5 to 4.5 or even higher than 4.8 interrupting the normal equilibrium of the healthy vagina.

In a particular embodiment of the present invention according to any one of the preceding embodiments, the condition of the invention does not comprise infectious diseases of the genitourinary apparatus. These infections disease might be sexually transmitted diseases and/or bacterial, fungal or yeast infections (e.g. candidiasis). These infection diseases might be characterized by bad-odour vaginal discharge, increased infectious vaginal flow, itching accompanied by yeast infection and other type of infectious vaginitis. More particularly, the condition of the invention does not include carcinogenic changes of neither the mucosa nor skin of the genitourinary apparatus.

The thinning of the urogenital mucosa results in different conditions or symptoms, as explained above collectively referred to as GS, such as one, some or all of vaginal dryness, post-coital bleeding, vaginal discharge, vaginal and/or vulvar discomfort, vaginal and/or vulvar pain, soreness, loss of sexual arousal and libido, itching, irritation, burning sensation, vulvar pruritus, dyspareunia, urinary urgency, increased frequency, nocturia, dysuria, urinary incontinence. Thus, in a particular embodiment of the present invention (i.e. first, second, third, and fourth aspect of the invention), the condition affecting the urogenital mucosa is GS. In a preferred embodiment of the present invention, the condition of the present invention is selected from the group consisting of one, more or all (preferably some or all) of vaginal dryness, post-coital bleeding, vaginal discharge, vaginal and/or vulvar discomfort, vaginal and/or vulvar pain, soreness, loss of sexual arousal and libido, itching, irritation, burning sensation, vulvar pruritus, dyspareunia, urinary urgency, increased frequency, nocturia, dysuria, urinary incontinence and combinations thereof. Amongst all this constellation of symptoms the more frequently found are: vaginal dryness, vaginal discomfort/pain, vulvar discomfort/pain, vaginal discharge, urinary urgency and urinary incontinence. Thus, preferably, the condition is selected from vaginal dryness, vaginal discomfort, vaginal pain, vaginal discharge, vulvar discomfort, vulvar pain, urinary urgency, urinary incontinence and combinations thereof.

More preferably, the condition is vaginal discharge and/or vaginal discomfort and/or vaginal pain and/or vulvar discomfort and/or vulvar pain.

As mentioned above, the urogenital mucosa is present in men and women, though a more extensive research has been done with women, as is the case of GSM and previous VVA. Thus, the subject of the present invention is a male or a female, more preferably a female.

GS affects peri- and post-menopause women and non-peri- and post-menopause women with estrogen deficiency, e.g. women who smoke or have been subjected to cancer treatment, oophorectomy, chemically-induced menopause, or sex-change treatments. Thus, in a particular embodiment of the present invention, the subject is selected from peri-menopause woman, post-menopause woman, smoker woman, or a woman subjected to cancer treatment, oophorectomy, chemically-induced menopause, or sex-change treatments.

As used herein, the term "prevent" or "prevention" means preventing, delaying and/or reducing the severity of the symptoms associated with the condition of the invention.

"Prophylactically effective amount" refers to an amount that when delivered, prevents, delays and/or reduces the severity of the symptoms associated with the condition of the invention.

"Treatment" refers to the reduction or elimination of the symptoms of the condition of the invention.

"Therapeutically effective amount" refers to an amount that is effective to reduce or eliminate the symptoms of the condition of the invention.

In a first aspect, the present invention refers to a composition comprising olive oil, trimethylglycine and xylitol (hereinafter referred to as composition of the invention) for use in the prevention and/or treatment of a medical condition affecting the urogenital mucosa.

Compositions comprising olive oil, TMG and xylitol are already known in the state of the art, see for example U.S. Pat. No. 8,540,970 B2. This patent describes the use of such compositions for the treatment of xerostomia. However, xerostomia and the conditions affecting the urogenital mucosa of the present invention, are conditions completely different. Furthermore, as shown in U.S. Pat. No. 8,540,970 B2 the treatment of xerostomy is due to an increase in the production of un-stimulated saliva and nothing in the state of the art suggests that this would prevent any condition of the urogenital mucosa from occurring, especially when no salivary glands are present in the urogenital tract.

Surprisingly, the composition of the present invention, comprising olive oil, TMG and xylitol, is useful for the prevention and/or treatment of a condition affecting the urogenital mucosa. The particular and preferred embodiments of the condition affecting the urogenital mucosa are the ones described above and applicable to all the aspects of the invention.

TMG has osmoprotective action and has no surfactant action. It should not be confused with the cocamidopropyl betaine (CAPB), being this one a detergent with surfactant action commonly used in oral hygiene products. In the composition of the present invention all detergents are excluded, specially taking into consideration that the group of patients encompasses a challenge to the mucosal integrity and detergents are totally deleterious in such case. Thus, in a particular embodiment, the composition of the present invention, according to any one of the embodiments of the present invention, does not comprise any detergent. Thus, the composition of the invention does not comprise sodium lauryl sulphate, sodium lauryl sarcosinate, CAPB, or detergents commonly used in hygiene products, preferably it does not comprise sodium lauryl sulphate, sodium lauryl sarcosinate and/or CAPB.

In a particular embodiment according to any one of the previous embodiments, the composition of the invention comprises 0.1%-5% by weight of olive oil, preferably 0.2%-4% by weight of olive oil, and more preferably 0.2%-2.5% by weight of olive oil.

All the percentages given in the present invention are given in weight by weight of the total composition (w/w), unless otherwise stated.

In a particular embodiment according to any one of the previous embodiments, the composition of the invention comprises 0.1%-10% by weight of TMG, preferably 1.5%-6% and more preferably 2%-4% by weight.

In a particular embodiment according to any one of the previous embodiments, the composition of the invention comprises 1%-50% by weight of xylitol, preferably 1%-30% and more preferably 1-15%, and even more preferably 10%.

In a preferred embodiment, the composition of the invention comprises 0.2%-4% by weight of olive oil, 1.5%-6% by weight of TMG and 1%-30% by weight of xylitol.

In another preferred embodiment, the composition of the invention comprises 0.2%-2.5% by weight of olive oil, 2%-4% by weight of TMG and 1%-15% by weight of xylitol.

As shown in the Examples, compositions comprising an amount of olive oil, TMG and xylitol within the ranges defined above are very effective in the treatment of a condition affecting the urogenital mucosa, such as GS. In another preferred embodiment, the composition of the invention comprises olive oil, TMG and xylitol in the amounts defined in any one of the formulations described in the Examples.

In a particular embodiment according to any one of the previous embodiments, olive oil is extra virgin olive oil. In another particular embodiment, the composition does not comprise any other vegetable oil, except essential oils. Like this, the use of oils of lower quality, e.g. palma oil, is avoided, since the use of these oils has been recently linked with highly significant increase and size of the metastasis of human oral carcinoma.

In a particular embodiment according to any one of the preceding embodiments, the composition comprises an anti-oxidant, preferably a natural antioxidant. Particularly, the antioxidant is selected from the group of tocopherol acetate, vitamin C, hydroxytyrosol, tyrosol, oleuropein, and mixtures thereof. Interestingly, hydroxytyrosol, tyrosol and oleuropein potentiate the anti-inflammatory, anti-bacterial and anti-oxidant activities of the olive oil, and appear to be able to stabilize the composition (i.e. reducing, or even eliminating, the need of further preservatives which will make the formulation more tolerable by the subjects). Thus, in a preferred embodiment the composition comprises hydroxytyrosol and/or tyrosol and/or oleuropein, preferably it comprises hydroxytyrosol, tyrosol and oleuropein.

In another particular embodiment according to any one of the previous embodiments, the composition of the invention further comprises one or more components selected from the group consisting of viscosity-controlling agents, moisturizing agents, preservatives, pH-regulating agents, sweeteners, proteolytic enzymes, emulsifiers, essential oils, cicatrizing agents, aromas, antioxidants, animal and/or plant gelatins, vegetal fibers, excipients, and a mixture thereof.

Preferably, the composition of the invention according to any one of the previous embodiments, comprises a cicatrizing, an antioxidant, a buffer, a preservative, a moisturizing and a solvent (preferably water); and optionally a rheological agent and/or an emulsifier. In a particular embodiment according to any one of the embodiments disclosed in the present paragraph, the composition comprises a sweetener, an aroma, an essential oil, vegetal fibers, animal and/or plant gelatins, a proteolytic enzyme or combinations thereof.

In another preferred embodiment according to any of the preceding embodiments, the composition of the invention does not comprise either of aroma, essential oil, abrasive agent, fluorine source or proteolytic enzyme. This embodiment facilitates tolerance by the patient.

These further components of the composition of the invention are commonly known by the skilled in the art, and non-limiting examples of said compounds are given below. In a particular embodiment according to any one of the preceding embodiments, these compounds are selected from the examples given below.

Any rheologic agent known in the state of the art can be used as viscosity-controlling agents. In particular, the rheologic agent can be selected from the group consisting of arabic gum, tragacanth gum, xanthan gum, carboxymethyl cellulose, carbopol-type polymers, pectins, mucines and mixtures thereof.

Any moisturizing agent known in the state of the art can be used in the composition of the invention. In particular, the moisturizing agent can be selected from the group consisting of glycerin, propylene glycol, sorbitol and mixtures thereof, preferably glycerin.

Among the preservatives that can be used in the composition of the invention, sodium benzoate, potassium sorbate, benzoic acid, diazolidinyl urea, imidazolinyl urea, sodium methylparaben, sodium propylparaben, and mixtures thereof are preferred.

In the composition of the invention any pH-regulating agent (also referred to as buffer) known in the state of the art can be used. In particular, the pH-regulating agent can be selected from the group consisting of lactic acid, lactates, citric acid, citrates, malic acid and salts thereof, sodium hydroxide, potassium phosphates, sodium phosphates, potassium pyrophosphate, sodium pyrophosphates and mixtures thereof.

Any sweetener known in the state of the art can be used in the composition of the invention. In particular, the sweetener can be selected from the group consisting of maltitol, isomaltitol, manitol, lactitol, sodium saccharine, acesulfame potassium, aspartame, cyclamate, taumatin, sucralose, estevia rebaudiana, neohesperidine DC and mixtures thereof.

Proteolytic enzymes such as papain, for example, can also be incorporated to the composition of the invention. This can be useful when mucosal injury lesions are present since it facilitates cleaning of the debris and reduces the dead cells that have been accounted for spurring the disruption of the mucosa.

Any suitable emulsifier known in the art can be used in the composition of the invention. In particular, the emulsifier can be selected from the group consisting of polyethylene glycol (PEG) 40 hydrogenated castor oil, lecithin and mixtures thereof.

As mentioned above, the composition of the invention can incorporate essential oils such as parsley seed oil and/or *Citrus medica* oil.

Any cicatrizing agent known in the state of the art can be used in the composition of the invention, in particular, selected from the group consisting of allantoin, D-panthenol, calcium pantothenate, and mixtures thereof.

The composition of the invention can comprise animal and/or plant gelatin such as bovine gelatin, fish gelatin, algae gelatin, and mixtures thereof.

The composition of the invention can also include aromas such as *Citrus medica* for example.

In another particular embodiment according to any of the previous embodiments, the composition of the invention does not comprise any additional active principle. In particular, it does not comprise honey and/or propolis.

According to the desired presentation/formulation, the composition includes all those components necessary to provide the desired organoleptic and rheologic form.

Preferably, the composition of the invention has pH between 3.5 and 6.5, preferably between 3.5 and 4.5. Preferably, water is used as a solvent, in particular in the case of liquid and doughy-gel like preparations.

During the treatment of the conditions of the present invention, an aqueous composition is preferred so the need for an emulsifier is reduced. Thus, in a preferred embodiment according to any one of the embodiments of the first aspect of the invention, the composition is an aqueous gel and it does not comprise an emulsifier.

In a particular embodiment, the composition of the invention is formulated as solution, gel, topical solution, topical ointment, topical gel, with or without applicator. Moreover, the composition is formulated as vaginal ovule. Furthermore, a single dose presentation (a monodosis vaginal ovule, for example) of the composition of the invention can be used.

In any case, the skilled in the art will formulate the composition of the invention in any suitable presentation that allows a simple use for the prevention and/or treatment of the condition of the invention.

The composition of the invention should be used daily along the duration of the condition of the invention and at least two weeks after the cessation of signs and symptoms.

A preferred administration protocol for the treatment of the condition of the present invention is to apply the composition of the invention vaginally, preferably with an applicator, or as a monodosis vaginal ovule. Like this, it can be easily applied in the affected areas.

Preferably the dosage is 2.5 to 5 ml per application. More preferably, the composition is administered before going to sleep, preferably laying down. As shown in the Examples, an application once per day is enough to get successful results. Thus, in a particular embodiment, the composition is applied once per day.

In a particular embodiment of the invention according to any one of the embodiments of the first aspect of the invention, the administration protocol is the one described in the Examples below.

A second aspect of the present invention refers to the use of a composition comprising olive oil, TMG and xylitol for the preparation of a medicament for the prevention and/or treatment of a medical condition affecting the urogenital mucosa.

The particular and preferred embodiments of the composition and condition of the invention described for the first aspect of the invention are applicable to the second aspect of the invention.

A third aspect of the present invention refers to a method of treating a medical condition affecting the urogenital mucosa in a subject in need thereof, comprising administering to the subject a therapeutically effective amount of a composition comprising olive oil, TMG and xylitol.

The particular and preferred embodiments of the composition and condition of the invention described for the first aspect of the invention are applicable to the third aspect of the invention. The subject is a male or a female, preferably a female.

In a particular embodiment of the third aspect of the invention, the method of treating a condition affecting the urogenital mucosa in a subject in need thereof, comprises administering to the subject a therapeutically effective amount of the composition of the invention as defined in any of the embodiments of the first aspect of the invention, said administration to the subject being commenced as soon as the first signs and symptoms appear. It is given daily, at least once per day, preferably once per day. In a preferred embodiment according to any one of the preceding embodiments, the dosage is 2.5 to 5 ml per application, administered with or without an applicator. More particularly, the composition is administered in the vagina and/or vulva.

In a preferred embodiment according to any one of the preceding embodiments of the third aspect of the invention, the composition is formulated as gel, more preferably topical gel, or as vaginal ovule, more preferably monodosis vaginal ovule. More preferably, the composition is administered before going to sleep, preferably laying down.

In a preferred embodiment, the protocol of administration of the composition of the invention is as described in any of the Examples below.

When the condition of the invention is GS, and said GS is due to cancer treatment, the administration of the composition of the invention is administered along the whole duration of the cancer treatment, and more preferably during at least two weeks more after the end of the cancer treatment.

A fourth aspect of the present invention refers to a method of preventing a medical condition affecting the urogenital mucosa in a subject which comprises administering to the subject a prophylactically effective amount of a composition comprising olive oil, TMG and xylitol.

The particular and preferred embodiments of the composition and condition of the invention described for the first aspect of the invention are applicable to the fourth aspect of the invention. The subject is a male or a female, preferably a female.

In a particular embodiment of the method of the fourth aspect of the invention, the administration to the subject commences as soon as possible:
- after being diagnosed with cancer and knowing when the cancer-therapy starts, and at least 24 hours before starting the oncologic treatment, when the condition is GS due to cancer treatment;
- after noting the first symptoms of menopause, when GS is due to peri-, post-menopause; or
- after the oophorectomy.

When the condition is GS due to cancer treatment, the composition should be administered during the whole cancer treatment, preferably without stopping between therapy cycles.

In a particular embodiment of the fourth aspect of the invention, the composition is given daily, at least once per day, preferably once per day. More particularly, the composition is administered before going to sleep, preferably laying down. In a preferred embodiment according to any one of the preceding embodiments, the dosage is 2.5 to 5 ml per application. The composition is administered with or without an applicator.

In a preferred embodiment according to any one of the preceding embodiments of the fourth aspect of the invention, the composition is formulated as gel, more preferably topical gel, or as vaginal ovule, more preferably monodosis vaginal ovule.

EXAMPLES

Specific embodiments of the invention that serve to illustrate the invention without limiting the scope thereof are described in detail below.

Example 1.—Study of Prevention of GS 1.1.—Aim and Subjects

The aim of the study was to compare the clinical efficacy of a composition according to the invention, i.e. comprising xylitol, olive oil and TMG, with a placebo composition without any of the mentioned ingredients in patients with GS, in particular in patients suffering from GS after oncological treatment. The particular GS conditions analysed were discomfort/pain in the vaginal and vulvar area and vaginal discharge.

20 patients were included in the study, and randomly divided into 2 groups.

1.2.—Inclusion and Exclusion Criteria

Inclusion

Patients that complained about vaginal discharge and discomfort/pain in the vaginal and vulvar area after treatment for breast cancer.

Exclusion

Patients that were using the tested products before starting the study were not allowed to participate. Those patients that did not comply with the inclusion criteria were excluded from the study.

1.3.—Formulations and Study Design:

Two different compositions were tested:

Composition A (Invention): comprising 0.5% Olive oil, 4.0% TMG and 10% Xylitol.

Composition B (Placebo): comprising the same excipients that in composition A but with none of the active ingredients.

| COMPOSITION A (Invention) | |
|---|---|
| Component | Percentage (w/w) |
| Olive oil | 0.50 |
| TMG | 4.00 |
| Xylitol | 10.00 |
| Other agents: rheological (1.1%), cicatrizing (0.05%), antioxidant (0.15%), pH regulating agent (2.5%), preservative (0.42%), moisturising (34.5%), water (46.78%). | 85.50 |

| COMPOSITION B (Placebo) | |
|---|---|
| Component | Percentage (w/w) |
| Olive oil | 0.00 |
| TMG | 0.00 |
| Xylitol | 0.00 |
| Other agents: rheological (1.1%), cicatrizing (0.05%), antioxidant (0.15%), pH regulating agent (2.5%), preservative (0.42%), moisturising (34.5%), water (61.28%). | 100.00 |

The study was crossover so everywoman used both compositions randomly assigned. Between the administration of one composition and the next one, there was one week of washout.

Products were packaged in white tubes identified with the number of patient. Content was kept in a closed envelope and only opened for data treatment.

Every complaint was assessed by a VAS (Visual analogue scale) 100 mm long.

VAS values resulted from vaginal discharge and vaginal discomfort/pain were obtained for every patient at four different days:

Day 0: at the beginning of the study.
Day 8: after first treatment period.
Day 15: after washout period.
Day 22: after second treatment period.

In all cases the products were applied vaginally as a fluid gel with an applicator dosing 5 ml. Patients applied 5 ml before going to bed every night during the whole week.

1.4.—Results and Conclusions

In the study there were two groups but at the time of expressing results, the groups were not taken into account. The results of the 20 patients are shown in Table 1 and Table 2.

Vaginal Discharge

The average results obtained after using the invention or the placebo compositions are shown in Table 1.

TABLE 1

|  | COMPOSITION | |
| --- | --- | --- |
|  | INVENTION | PLACEBO |
| Average | 31.65 | 51.9 |
| p | <0.000 | |

Vaginal Discomfort/Pain

The average results obtained after using the invention or placebo compositions are shown in Table 2:

TABLE 2

|  | COMPOSITION | |
| --- | --- | --- |
|  | INVENTION | PLACEBO |
| Average | 36.7 | 53.5 |
| p | <0.000 | |

As shown in Tables 1 and 2, the composition according to the invention, significantly reduces vaginal discomfort/pain (p<0.000) and vaginal discharge (p<0.000) in comparison with the placebo composition, in a group of 20 women when applied vaginally once a day for a week.

Example 2.—Comparative Study of Treatment of GS 2.1.—Objective, Subjects and Formulations The objective of the study was to compare the clinical efficacy of a composition according to the invention (i.e. comprising including xylitol, olive oil and TMG as active ingredients), with a composition comprising only olive oil as active ingredient, in patients with GS, in particular in patients with GS after oncological treatment. The particular GS conditions analysed were discomfort/pain in the vaginal and vulvar area and vaginal discharge.

For the purpose of the study 9 patients were accepted into the study. Patients were randomly divided into 2 groups (one group with 4 patients and another one with 5 patients).

2.2.—Inclusion and Exclusion Criteria

Inclusion Criteria

Patients that complained from vaginal discharge and discomfort/pain in the vaginal and vulvar area after treatment for breast cancer.

Exclusion Criteria

Those patients who did not comply with the inclusion criteria were excluded from the study.

2.3.—Formulations and Study Design

Two different compositions were tested.

Composition A (invention), comprising 0.5% Olive oil, 4.0% TMG and 10% Xylitol.

Composition B (olive oil), comprising 0.5% Olive oil, without TMG and without Xylitol.

| COMPOSITION A (Invention) | |
| --- | --- |
| Component | Percentage (w/w) |
| Olive oil | 0.50 |
| TMG | 4.00 |
| Xylitol | 10.00 |
| Other agents: rheological (1.1%), cicatrizing (0.05%), antioxidant (0.15%), pH regulating agent (2.5%), preservative (0.42%), moisturising (34.5%), water (46.78%). | 85.50 |

| COMPOSITION B (Olive oil) | |
| --- | --- |
| Component | Percentage (w/w) |
| Olive oil | 0.50 |
| TMG | 0.00 |
| Xylitol | 0.00 |
| Other agents: rheological (1.1%), cicatrizing (0.05%), antioxidant (0.15%), pH regulating agent (2.5%), preservative (0.42%), moisturising (34.5%), water (60.78%) | 99.50 |

The study was crossover so everywoman used both compositions randomly assigned. Between the administration of one composition and the next one, there was one week of washout.

Products were packaged in white tubes identified with the number of the patient. Content was kept in a closed envelope and only opened for data treatment.

Every complaint was assessed by a VAS 100 mm long.

VAS values resulted from vaginal discharge and vaginal discomfort/pain were obtained for every patient at four different days:

Day 0: at the beginning of the study.
Day 8: after first treatment period.
Day 15: after washout period.
Day 22: after second treatment period.

In all cases the product was applied vaginally as a fluid gel with an applicator dosing 5 ml. Patients applied 5 ml before going to bed every night during the whole week.

2.4.—Results and Conclusions

In the study there were two groups but at the time of expressing results, the groups were not taken into account.

Vaginal Discharge

The average results after using the invention or olive oil compositions are shown in Table 3:

TABLE 3

|  | INVENTION | OLIVE OIL |
| --- | --- | --- |
| Average | 30.22 | 50.56 |
| p | 0.003 | |

Vaginal Discomfort/Pain

The average results obtained after using the invention or olive oil compositions are shown in Table 4:

TABLE 4

|  | INVENTION | OLIVE OIL |
|---|---|---|
| Average | 27.44 | 47.33 |
| p | 0.01 | |

As shown in Tables 3 and 4, the composition of the invention, significantly reduces vaginal discharge (p=000.3) and vaginal discomfort/pain (p=0.01) in comparison with the composition comprising only 0.5% olive oil as active ingredient, in a group of 9 women when applied vaginally once a day for a week.

The invention claimed is:

1. A method of treating genitourinary syndrome characterized by a thinning of the urogenital mucosa in a human in need thereof, consisting essentially of administering a composition consisting essentially of olive oil, trimethylglycine, and xylitol to said human in need thereof to effectively treat the genitourinary syndrome characterized by a thinning of the urogenital mucosa in the human in need thereof.

2. The method according to claim 1, wherein the olive oil is present in the composition at 0.1%-5% by weight.

3. The method according to claim 1, wherein the trimethylglycine is present in the composition at 0.1%-10% by weight.

4. The method according to claim 1, wherein the xylitol is present in the composition at 1%-50% by weight.

5. The method according to claim 1, wherein the composition is formulated as a gel or as a vaginal ovule.

6. The method according to claim 1, wherein the composition consists essentially of 0.1%-5% by weight of olive oil, 0.1%-10% by weight of trimethylglycine, and 1%-50% by weight of xylitol.

7. A method of treating genitourinary syndrome characterized by a thinning of the urogenital mucosa in a human in need thereof, consisting essentially of administering a composition consisting essentially of olive oil, trimethylglycine, xylitol, and an antioxidant selected from the group consisting of hydroxytyrosol, tyrosol, oleuropein and mixtures thereof to said human in need thereof to effectively treat the genitourinary syndrome characterized by a thinning of the urogenital mucosa in the human in need thereof.

8. The method according to claim 7, wherein the olive oil is present in the composition at 0.1%-5% by weight.

9. The method according to claim 7, wherein the trimethylglycine is present in the composition at 0.1%-10% by weight.

10. The method according to claim 7, wherein the xylitol is present in the composition at 1%-50% by weight.

11. The method according to claim 7, wherein the composition is formulated as a gel or as a vaginal ovule.

12. The method according to claim 7, wherein the composition consists essentially of 0.1%-5% by weight of olive oil, 0.1%-10% by weight of trimethylglycine, and 1%-50% by weight of xylitol.

* * * * *